(12) United States Patent
Saito

(10) Patent No.: US 8,507,258 B2
(45) Date of Patent: Aug. 13, 2013

(54) APPARATUS FOR PERFORATING MEMBRANE

(75) Inventor: Takashi Saito, Tokyo (JP)

(73) Assignee: Akita Prefectural University, Akita-shi (JP)

( * ) Notice: Subject to any disclaimer, the term of this patent is extended or adjusted under 35 U.S.C. 154(b) by 564 days.

(21) Appl. No.: 11/945,983

(22) Filed: Nov. 27, 2007

(65) Prior Publication Data

US 2008/0176314 A1    Jul. 24, 2008

Related U.S. Application Data

(62) Division of application No. 10/070,157, filed as application No. PCT/JP00/06045 on Sep. 6, 2000, now Pat. No. 7,320,885.

(30) Foreign Application Priority Data

Sep. 9, 1999  (JP) .................................. 11-255024

(51) Int. Cl.
*C12M 1/00*    (2006.01)

(52) U.S. Cl.
USPC .................................. 435/285.1; 435/283.1

(58) Field of Classification Search
USPC .................... 435/285.1, 446, 173.2; 600/108
See application file for complete search history.

(56) References Cited

U.S. PATENT DOCUMENTS

| 4,736,743 | A | * | 4/1988 | Daikuzono | 606/28 |
|---|---|---|---|---|---|
| 5,193,526 | A | * | 3/1993 | Daikuzono | 606/15 |
| 5,445,608 | A |   | 8/1995 | Chen |   |
| 5,446,157 | A |   | 8/1995 | Morgan |   |
| 5,836,940 | A | * | 11/1998 | Gregory | 606/15 |
| 5,876,989 | A |   | 3/1999 | Berg |   |
| 5,972,667 | A | * | 10/1999 | Conia et al. | 435/173.2 |
| 6,753,171 | B2 |   | 6/2004 | Karube |   |
| 2001/0005791 | A1 | * | 6/2001 | Ginsburg et al. | 607/106 |

FOREIGN PATENT DOCUMENTS

| GB | 2 209 468 A | 5/1989 |
|---|---|---|
| JP | 59-082084 A | 11/1984 |
| JP | 02-186993 A | 7/1990 |
| JP | 04-166081 A | 11/1992 |
| JP | 05-049483 A | 2/1993 |

(Continued)

OTHER PUBLICATIONS

Altin, J.G., et al., "Testing the In Vivo Role of Protein Kinase C and c-Fos in Neurite Outgrowth by Microinjection of Antibodies Into PC12 Cells," Molecular Biology of the Cell 3:323-333, Mar. 1992.

(Continued)

*Primary Examiner* — Michael Hobbs
(74) *Attorney, Agent, or Firm* — Christensen O'Connor Johnson Kindness PLLC

(57) ABSTRACT

A method of perforating a membrane and an apparatus therefor is presented. The method includes bringing a membrane-denaturing substance into contact with or close proximity to at least a site of the membrane, the substance inducing a membrane-denaturing reaction by a stimulus; providing the stimulus to the substance so as to denature the membrane; and perforating the membrane with a membrane-destroying member. The stimulus is carried through the membrane-destroying member. The present invention eliminates the influence of the membrane-denaturing agent on the substance to be injected into the cell. The present invention also enables applying the stimulus locally, with a simple construction.

18 Claims, 6 Drawing Sheets

(56) References Cited

FOREIGN PATENT DOCUMENTS

| | | |
|---|---|---|
| JP | 08322548 A | 12/1996 |
| WO | 96/07432 A1 | 3/1996 |
| WO | WO 99/046361 * | 9/1999 |

OTHER PUBLICATIONS

Bataillé, N., et al., "Cytoplasmic Transport of Ribosomal Subunits Microinjected Into the *Xenopus laevis* Oocyte Nucleus: A Generalized, Facilitated Process," Journal of Cell Biology 111:1571-1582, Oct. 1990.

Boch, R., et al., "Study of Photoinduced Energy and Electron Transfer in α-Terthienyl-Bovine Serum Albumin Conjugates: A Laser Flash Photolysis Study," Photochemistry and Photobiology 64(1):92-99, 1996.

Hamill, O.P., et al., "Improved Patch-Clamp Techniques for High-Resolution Current Recording From Cells and Cell-Free Membrane Patches," Pflügers Archiv—European Journal of Physiology 391:85-100, 1981.

Haydon, P.G., et al., "Membrane Deformation of Living Glial Cells Using Atomic Force Microscopy," Journal of Microscopy 182(Pt. 2):114-120, May 1996.

Henriksen, G.H., and S.M. Assmann, "Laser-Assisted Patch Clamping: A Methodology," Pflügers Archiv—European Journal of Physiology 433:832-841, 1997.

Horn, R., and A. Marty, "Muscarinic Activation of Ionic Currents Measured by a New Whole-Cell Recording Method," Journal of General Physiology 92:145-159, Aug. 1988.

Kasuya, T., and M. Tsukakoshi, "Gene Transfection by Laser Cell Surgery," Review of Laser Engineering 15(8):41-52, Aug. 1987.

Kitayama, A., and Y. Kawakami., "Injection of DNA Into Bacteria Using Electroporation Method," Chemical Engineering 35(12):944-948, 978, Dec. 1990.

Kimura, N., et al., "Development of Laser-Based Cell Processor," O plus E, Apr. 1989, No. 13, pp. 100-103.

Knoblauch, M., et al., "A Galinstan Expansion Femtosyringe for Microinjection of Eukaryotic Organelles and Prokaryotes," Nature Biotechnology 17:906-909, Sep. 1999.

Kurata, S.-I., et al., "The Laser Method for Efficient Introduction of Foreign DNA Into Cultured Cells," Experimental Cell Research 162:372-378, 1986.

Laffafian, I., and M.B. Hallett, "Lipid-Assisted Microinjection: Introducing Material Into the Cytosol and Membranes of Small Cells," Biophysical Journal 75:2558-2563, Nov. 1998.

Levitan, E.S., and R.H. Kramer, "Neuropeptide Modulation of Single Calcium and Potassium Channels Detected With a New Patch Clamp Configuration," Nature 348:545-547, Dec. 1990.

Madsen, S., et al., "Oxidation of Hydrogen-Passivated Silicon Surfaces by Scanning Near-Field Optical Lithography Using Uncoated and Aluminum-Coated Fiber Probes," Journal of Applied Physics 82(1):49-53, Jul. 1997.

Marles, R.J., "Thiophenes as Mosquito Larvicides: Structure—Toxicity Relationship Analysis," Pesticide Biochemistry and Physiology 41:89-100, 1991.

Matsue, T., et al., "Microring-Ring Electrode for Manipulation of a Single Cell," Biochimica et Biophysica Acta 1157:332-335, 1993.

Matsumoto, N., et al., "Development of Micro Electroporation System for Single Cells," T. IEE Japan 116E(5):184-189, 1996.

"Membrane," Merriam-Webster's Collegiate Dictionary, 10th ed., 1997, p. 724.

Saito, T., et al., "Photosensitizing Applied Microinjection," Proceedings of the 14th Symposium on Biological and Physiological Engineering (BPES'99), Japan, 14:77-80, 1999.

Saito, T., et al., "Light Dose and Time Dependency of Photodynamic Cell Membrane Damage," Photochemistry and Photobiology 68(5):745-748, 1998.

Sambrook, J., et al., Molecular Cloning: A Laboratory Manual, 2d ed., Cold Spring Harbor Laboratory Press, Cold Spring Harbor, N.Y., 1989, vol. 3, Chap. 16, "Expression of Cloned Genes in Cultured Mammalian Cells," pp. 16.30-16.31, 16.48-16.53.

Thorpe, W.P., et al., "Dynamics of Photoinduced Cell Plasma Membrane Injury," Biophysical Journal 68:2198-2206, May 1995.

Valenzeno, D.P., "Photomodification of Biological Membranes With Emphasis on Singlet Oxygen Mechanisms," Photochemistry and Photobiology 46(1):147-160, 1987.

Specht, K.G. and M.A.J. Rodgers, "Depolarization of Mouse Myeloma Cell Membranes During Photodynamic Action," Photochemistry and Photobiology, Great Britain, 51(3): 319-324, 1990.

\* cited by examiner

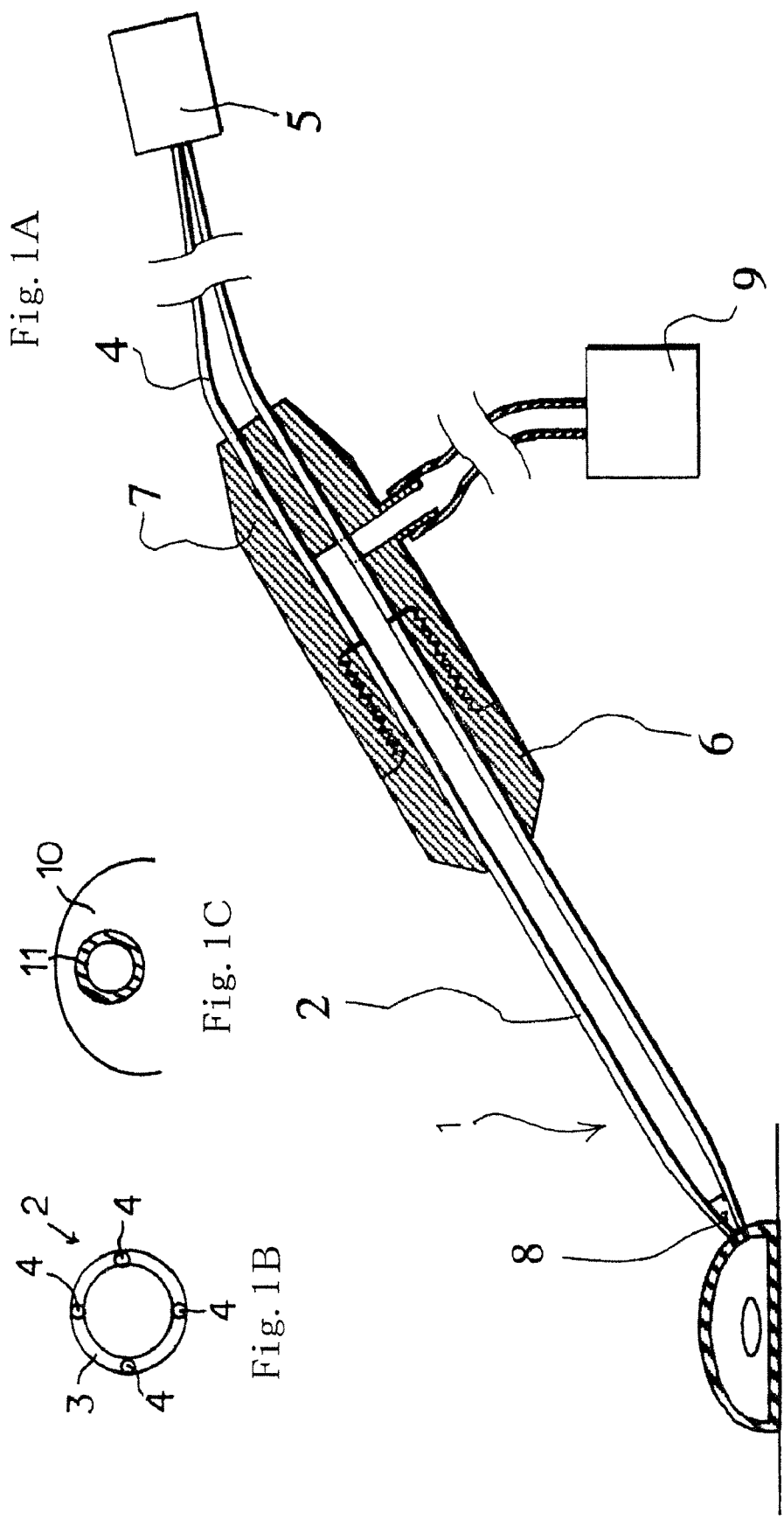

APPARATUS FOR PERFORATING MEMBRANE

CROSS-REFERENCE TO RELATED APPLICATION

This application is a divisional of U.S. application Ser. No. 10/070,157, now U.S. Pat. No. 7,320,885, which is a National Stage of International Application No. PCT/JP00/006045, filed Sep. 6, 2000, the disclosure of which is incorporated by reference herein.

TECHNICAL FIELD

This invention relates to a method and apparatus for perforating a membrane by partially treating the membrane such as cell membrane, with a membrane-denaturing agent, etc. It also relates to a microinjection apparatus using the method for perforating the membrane.

BACKGROUND OF THE INVENTION

In gene therapy and artificial substance production systems using living organisms, means of introducing a nucleic acid, a protein, and such, into the interior of a cell are extremely important. On the other hand, techniques for extracting structures such as the nucleus of a cell, are also gaining wide attention. Therefore, it can be said the injecting and extracting substances into/from cells, the basic unit constituting organisms, is a fundamental technique of bioengineering.

In the prior art, the method of destroying or perforating the membrane depends on a physical shearing force. However, cell membrane destroying using the shear force of a capillary requires skilled experience on the part of manipulator. Also, in many cases, the capillary cannot be inserted into the cell membrane of normal cells, except large size egg cells, due to the flexibility of the cell membrane. In this regard, as a method that does not depend on the physical shear force, a method of denaturing a membrane with a substance (a membrane-denaturing agent) inducing a membrane-denaturing reaction is presented (PCT/JP99/01223). The membrane-denaturing agent is a substance that induces the membrane-denaturing reaction by a selected specific stimulus as a trigger. By controlling a degree of membrane denaturation, a perforating method allowing the self-repairing of the perforated membrane can be provided.

According to the method, the membrane-denaturing agent must be in contact with the cell or close thereto. In one embodiment, a photosensitizer as a membrane-denaturing agent is in contact with a site of cell via a capillary, and light is applied to the cell-neighboring area as a whole (for example, a circular region of about 100 micrometers including the cell contacting the capillary).

In this method, the light exposure is introduced such that an area including the capillary that contacts the membrane-denaturing agent is exposed. Therefore, if the capillary is filled with a mixture of a substance to be injected into the cell and the membrane-denaturing agent, the membrane-denaturing agent within the capillary as well as the membrane-denaturing agent on the tip of the capillary may be activated by the light application, thereby generating reactive oxygen species.

If the substance filled in the capillary to be injected into the cell is a chemically vulnerable substance such as genes and such, the substance may be damaged by the reactive oxygen species.

To avoid such damage, a light application method that allows a pinpoint light application to the tip of capillary may be employed. However, the method has disadvantages in that a light focus adjusting mechanism that follows the movement of the tip of capillary should be required and it makes the apparatus costly.

Therefore, the present invention relates to an improvement of the membrane-denaturing method with a membrane-denaturing substance inducing the membrane-denaturing reaction. An object of the present invention is to eliminate the influence of membrane-denaturing agent to the substance to be injected into the cell as low as possible.

Objects of the present invention are not limited to the above-mentioned object. For example, when the capillary or intracellular sensor is used in a tissue in vivo and such, it is difficult to apply stimulus such as the light to the tip of the capillary or sensor locally. Another object of the present invention is to provide a method and apparatus that enable locally applying the stimulus, with a simple construction.

SUMMARY OF THE INVENTION

Techniques of the present invention is characterized by carrying a stimulus to be introduced to a membrane-denaturing substance via a supporting member for supporting the membrane-denaturing substance, or a membrane-destroying member for destroying the membrane, or other stimulus carrying member. By carrying a stimulus through a certain member, the stimulus can locally be introduced to a selected site. Though the supporting member, the membrane-destroying member and the stimulus-carrying member may be of individual elements, in one preferred aspect, the membrane-supporting member, the membrane-destroying member and the stimulus-carrying member are the same element.

A combination of a stimulus and a membrane-denaturing agent inducing the membrane-denaturing reaction by the stimulus, important constituting elements of the present invention, will be described based on light and a photosensitizing agent, a preferred example of such combination. As a method of partially and temporarily denaturing and/or disrupting the membrane other than the physical shear force, the phospholipid radical chain peroxidation came into attention. Reactive oxygen species such as singlet oxygen, and superoxide radicals peroxidize unsaturated phospholipids of the cell membrane by chain reactions. As countermeasures, cells have radical scavengers such as α-tocopherol (vitamin E), and L-ascorbic acid, a water soluble anti-oxidant, (vitamin C), superoxide dismutase (SOD) and such oxidation defense mechanism, to resist oxidation. When such chain peroxidation exceeds the oxidation defense capacity, phospholipid membrane disruption progressed rapidly in an exponential manner, and the cell becomes unable to maintain metabolism as the membrane loses its ion barrier function. If these chain reactions progress further, the cell will finally die.

Photosensitizers (PS) are molecules that trigger such lipid chain peroxidation by producing reactive oxygen species using light. Rose Bengal, porphyrin, and such can be given as photosensitizers in general use. By utilizing such photosensitizers as membrane-denaturing agents, when denaturing the membrane, it will be sufficient to conduct chain peroxidation partially on the minimum objective cell surface, for a short period of time. Furthermore, the membrane damaged by the chain peroxidation at the time of membrane perforation, is expected to be repaired after the perforation by the fluidity of the membrane itself, or by the aforementioned anti-oxidation systems. Thus, by controlling an amount of the photosensitizers or an exposure time of the light, a degree of membrane denaturation can be controlled, a perforation can easily be done, and the membrane can be repaired without causing cell death.

As a preferable combination of the membrane-denaturing agent and stimulus, the combination of the light and the photosensitizer was explained. However, the combination of the membrane-denaturing agent and stimulus used for denaturing or perforating the membrane can be selected as any combination, as long as it can perforate the membrane in a controllable manner, without completely destroying the membrane.

In one preferred embodiment, the membrane-denaturing agent is a photocatalyst such as titanium oxide, and the stimulus is the light that activates the photocatalyst (ultraviolet ray in case of titanium oxide). The photocatalyst promotes generation of reactive oxygen species with the light exposure. The cell membrane is oxidized with the reactive oxygen species and fluidity and flexibility of the membrane are reduced.

The stimulus of the present invention must be carried through the supporting member, the membrane-destroying member or the stimulus-carrying member. Preferably, the stimulus can be selected from the group comprising light, electricity, heat, and oscillations. If the stimulus is the light, the supporting member, the membrane-destroying member or the stimulus carrying member may be made of materials that allows the transmission of wavelengths inducing the membrane-denaturing reaction. For example, such material is selected from soda glass, quartz glass, acrylic resin, or styrole resin. If the stimulus is the heat, the supporting member, the membrane-destroying member or the stimulus carrying member may be made of materials having a good heat conductivity, such as gold, platinum, tungsten, aluminum, copper, any alloy of the mentioned metals, and ceramic material, for example. If the stimulus is the electricity, the supporting member, the membrane-destroying member or the stimulus carrying member may be made of materials having a good electric conductivity, such as gold, platinum, tungsten, aluminum, copper, any alloy of the mentioned metals, conducting polymer including polypyrrole and polythiophene, or carbon materials including carbon nanotube.

The stimulus used for the present invention is not limited to the above-mentioned examples. The stimulus includes electromagnetic waves including light, particle rays including radiation, heat, cooling, electricity, magnetism, oscillations including ultrasonic waves, physical contact, chemical substances, as well as living beings including the cell (white blood cell, for example), and viruses, or any combinations thereof. For example, a light-emitting element is provided at the tip of the capillary, an example of supporting member or membrane destroying member, and the power for emitting the element can be carried via the capillary.

As the substance (mainly compounds) that are used to denature and perforate the membrane, enzymes involved in membrane denaturation and disruption, antibody molecules, membrane bound proteins, glycoproteins, lipids, and such may be used. The photosensitizers such as porphyrin, rose Bengal, methylene blue, acid red, alpha-terthienyl, etc., or their derivatives may also be used. Oxidants such as reactive oxygen species, reductants, explosive compounds such as nitroglycerin/picric acid, magnetic particles/magnetic fluids, metal particles/semiconductor particles/insulator particles/ photoelectric converting elements/piezoelectric elements, and such may also be suitably used. These compounds may be used alone or together with others.

Specifically, the supporting member, the membrane-destroying member or the stimulus-carrying member are a capillary (including a capillary having an optical fiber disclosed in the embodiment), an intracellular sensor, and such. In the specification, the capillary means a micro tubular member including the capillary made of glass, and the materials of the capillary are not limited. Also, the supporting member, the membrane-destroying member or the stimulus carrying member is not limited to the capillary and may be crystals, macro compounds such as $C_{60}$, micro pipettes, glass micro electrodes, patch electrodes, metal micro electrodes, wires, crystal whiskers, living organisms including cells, magnetic particles/magnetic fluids, metal particles/semiconductor particles/insulator particles/piezoelectric elements, micro structures such as micro machines, as well as objects in which these are conjugated.

The forms of the supporting member, the membrane-destroying member or the stimulus-carrying member may not be limited. It may be kenzan (needlepoint flower holder)-shaped, spherical, needle-shaped, rod-shaped, tube-shaped, or may be provided in a combined shape thereof. Examples of tube-shaped supports are, specifically, pipettes, tubes, injection needles, and such. Spherical supports may be beads that can be handled by the laser tweezers technique. As to the supporting member for supporting the membrane-denaturing substance, a supporting site for supporting the membrane-denaturing substance (membrane denaturation accelerating site) may be on the support surface or may be a part of the surface, depending on the purposes (in case that the supporting member is a bead for example, such site may be a whole spherical surface, or a selected site.). When coating or fixing the membrane-denaturing substance to the supporting member, the methods that could be used are, solvent evaporation drying, sputtering, vacuum deposition, plasma polymerization, chemisorption, physisorption, radical polymerization, ion polymerization and such. The supporting member may be filled with the membrane-denaturing agent (for example, the supporting member is the capillary and the membrane-denaturing agent is filled inside the capillary).

According to the present invention, the stimulus should be carried via the supporting member, the membrane-destroying member or the stimulus-carrying member. Thus, desirably, the transmission direction of the stimulus should be controlled. As a direction-controllable stimulate, preferable examples are the light and the electricity. It will be explained in case that the membrane destroying member and the supporting member are the capillary for example. In case of light, if the capillary incorporated with an adequate reflection layer with a known optical fiber technique is used, the light transmits through the sidewall of the capillary in the extending direction thereof without the light leakage problem. In case of electricity, the direction of transmission can be controlled by providing an electrically insulating layer on a conductive layer and a site that is to be contact with the cell is not provided with the electrically insulating material. Also, in case of heat, the heat stimulus can be employed if a thermally insulating layer can be provided on a thermally conductive layer. In addition, a mechanical stimulus such as a super sonic vibration may be employed. For example, the following technique may be employed in which providing a microcapsule containing the cell membrane destroying agent, destroying the capsule with the vibration via the supporting member, and releasing the membrane-destroying agent.

The membrane may be a membrane containing photoelectric converting elements and piezoelectric elements, or may be cell membrane or cell wall of animals/plants, biomembranes, or artificial membranes. As a biomembrane, a cell coat including cell wall, cell membrane including intracellular cell membrane, nucleus membrane, viral membrane, cytoplasmic microtuble, microsome membrane, golgi apparatus membrane, lysosome membrane, endoplasmic reticulum membrane, tonoplast membrane, peroxysome membrane, plastid membrane, ribosome membrane, mitochondrial membrane, and such can be given. Examples of artificial membranes are protein membranes, lipid membranes, polymer membrane such as collagen, metal membranes, semiconductor membranes, insulator membranes, conductive polymer membranes such as polyacetylene, polythiophene, and such.

Substances that are to be injected can be any substances that could not permeate the membrane easily by normal diffusion, or substances that are to be passed through the membrane artificially in large amounts. Specific examples are nucleic acids, proteins, lipids, membrane structures, and artificial substances such as micro machines and magnetic particles. Optionally, a carrier could be injected together with the substances to be injected. The carriers are gases, liquids, or solids that can be used to dissolve, or suspend the substance to be injected. Examples of carriers are buffers and such in which nucleic acids are dissolved.

BRIEF DESCRIPTION OF THE DRAWINGS

FIG. 1A is a schematic view showing a preferred embodiment of a microinjection apparatus;

FIG. 1B shows locations of an end wall of a sidewall of capillary and optical fibers;

FIG. 1C shows a denatured site formed on a membrane;

PREFERRED EMBODIMENTS FOR CARRYING OUT THE INVENTION

Figure 2A:
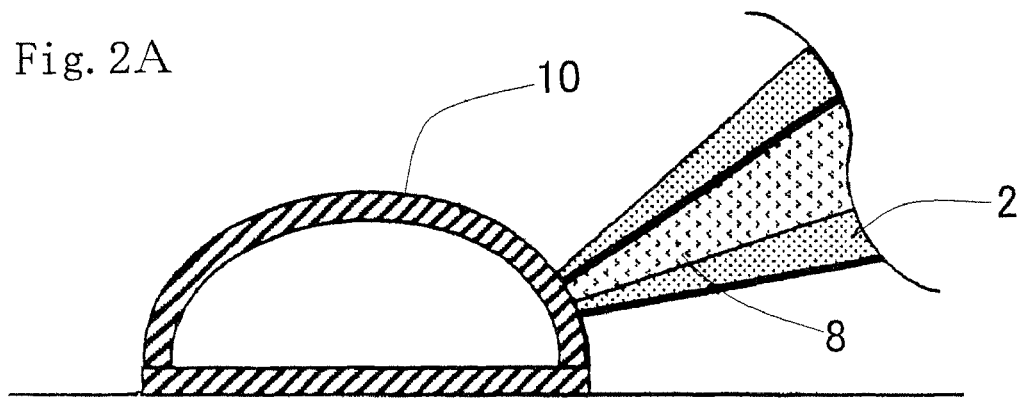
FIGS. 2A-D show a process of injecting a tip of a capillary into a cell membrane.
Figure 2B:
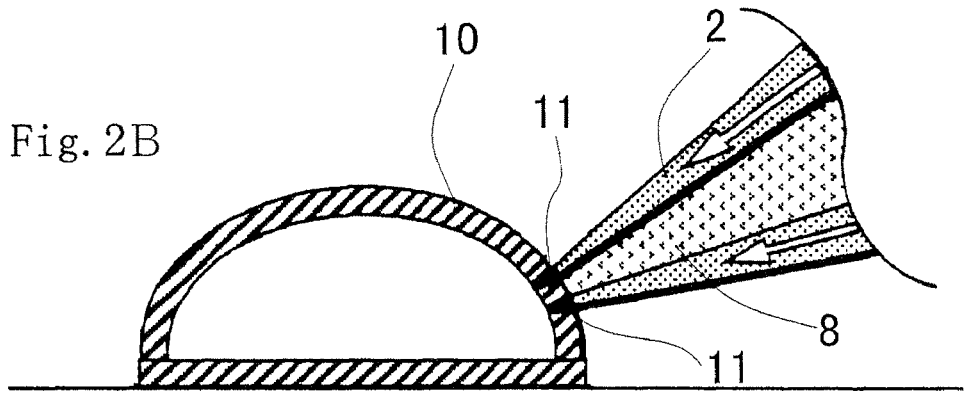
Figure 2C:
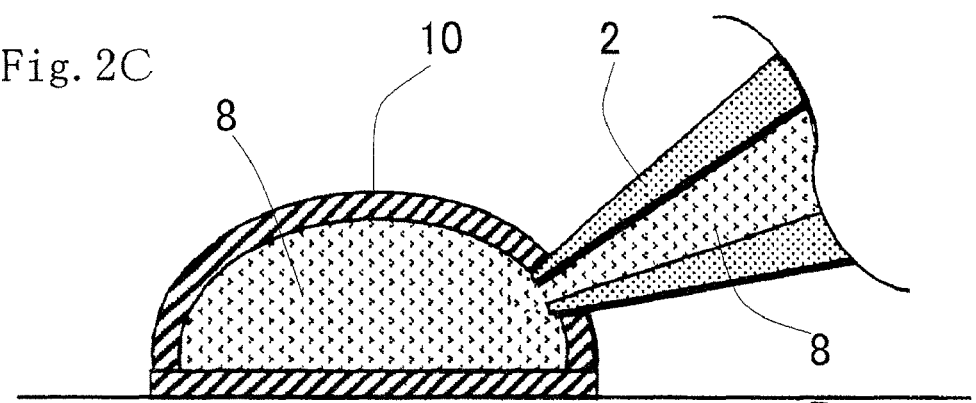
Figure 2D:
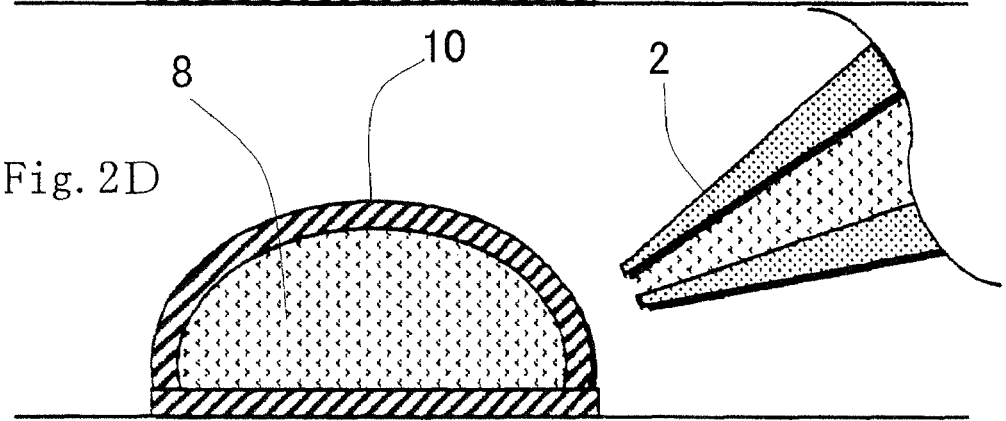

FIGS. 1A-C are schematic views showing a preferred embodiment of a microinjection apparatus employing the present invention. According to the embodiment, the light is selected as the stimulus, and the photosensitizer agent is selected as the membrane-denaturing agent.

Referring to FIGS. 1A-C and 4, the microinjection apparatus includes a capillary 1, a common member, which constitutes a membrane-destroying member, a supporting member for supporting the membrane-denaturing agent, a stimulus-carrying member, and an injection member for injecting a pre-selected substance. A distal end of the capillary 1 is tapering, and an opening diameter of the tip of capillary is several hundred nanometers. At a proximal end of the capillary 1, optical fibers 4 are provided and opposed to an end wall 3 of a sidewall 2 of the capillary 1. A proximal end of the optical fibers 4 are provided with a light source 5, and the light from which transmits through the optical fibers 4 and is supplied to the end wall 3 of the side wall 2 of the capillary 1 in the direction of the length of the side wall 2 toward the tip of the capillary 1. The light is carried to the tip of the capillary 1 through the sidewall 2 as a light guide.

In the figures, four optical fibers 4 opposed to the end wall 3 and uniformly spaced in the circumferential direction are disclosed. The number of the optical fibers 4 is not limited to four, and it may be three or less than three, or five or more than five.

An outer circumferential surface of the sidewall 2 of the capillary 1 is provided with a short cylindrical bracket 6 at the proximal end. The outer wall of the bracket 6 has a site on which is threads are formed. Threads that are threaded to the threads on the bracket are formed in an inner wall of a cylindrical supporter 7 at an opening end that supports the optical fibers 4. When the supporter 7 is connected to the bracket 6, the distal end of the optical fibers 4 are opposed and in proximity to the end wall 2 of the sidewall of the capillary 1.

Inside the capillary 1, an injection liquid 8 including the photosensitizer (the injection liquid contains substance to be injected into the cell, such as gene) is filled. The apparatus is provided with pressure means 9 that introduces pressure to an inner space of the capillary 1.

Figure 3:
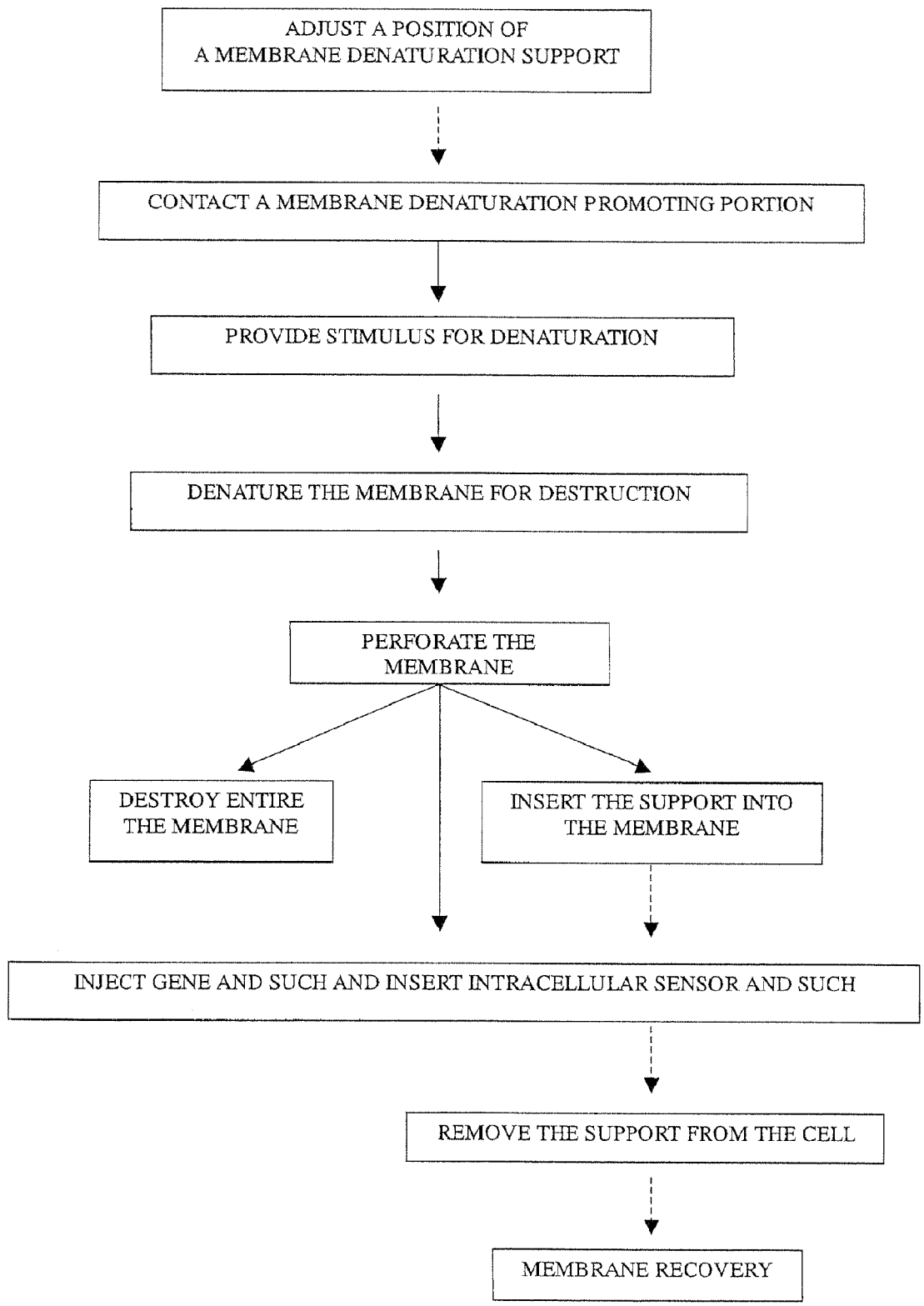
FIG. 3 is a flow chart showing a membrane perforating technique.

A method of injecting the desired substance into the cell with above-constructed microinjection apparatus will be described in conjunction with the FIGS. 1A-C, 2A-D and 3. FIGS. 2A-D show the membrane member and only the distal site of the capillary. As shown in FIGS. 1A-C and 2A-D, reference numeral 10 denotes a cell membrane as an example of membrane structure. FIG. 3 is a flow chart showing the microinjection technique. In FIG. 3, the capillary 1 is described as the supporting member.

Referring to FIGS. 1A-C and 2A, during the injection operation, the capillary 1 is in contact with the cell membrane 10 at a low speed (7 micrometer/sec, for example) so that the tip of the capillary does not perforate the cell membrane 10 physically. In this state, the injection liquid 8 containing the photosensitizer is ejected onto the cell membrane 10 (see FIG. 2B). The photosensitizer contacts the cell membrane and then diffuses. Because the activated oxygen can be diffused to a certain distance after generation thereof, the denaturing effect can be obtained even if the membrane is spaced from where the activated oxygen is generated (a few micrometers, for example). Therefore, the photosensitizer, as the membrane denaturing substance, does not necessarily directly contact the membrane. Means for introducing the injection liquid containing the photosensitizer is not limited to the forcible means with pressure means. It may be effected on the cell by the natural diffusion. Also, in place of pressuring, an injection by an electric current such as electroporesis may be used.

Referring to FIGS. 1A-C and 2A-D, at the same time, the light stimulus supplied from the light source 5 is introduced to the side wall 2 of the capillary from the end wall 3 of the side wall 2 of the capillary 1, and then carried to the tip of the capillary 1 though the side wall 2 as a light guide. Then the light is applied from the distal end of the sidewall 2. Only an exposed site within the cell membrane 10 that is in contact with the photosensitizer is denatured by the photosensitizer to form a membrane-denatured site 11.

Referring to FIGS. 1A-C and 2C, because the membrane-denatured site 11 is deteriorated and its flexibility is reduced, by moving the capillary 1 at a low speed, the tip of the capillary 1 is easily injected into the cell membrane. In this state, the liquid 8 containing the photosensitizer is injected into the cell membrane with the pressure means 9. Then, the tip of the capillary 1 is removed from the cell membrane, and the perforated cell membrane 10 will recover by itself to return to the original state (see FIG. 2D).

According to the embodiment, the capillary 1 on the market that does not have a clad layer was used, and in fact the light may leak from the sidewall 2. However, the leakage site is concentrated on a transitional bent site (5 mm from the tip) of the sidewall 2 between a straight site and a tapering site. Because the volume of the liquid that is to be injected into the cell is very small amount, an influence of the leakage site is not significant. In this regard, if the membrane-destroying member (supporting member) is constructed from the micro capillary-shaped optical fiber, which may be made of the ordinary optical fiber extended and sharpen by the heating process similar to the capillary, the light leakage problem may be eliminated.

Figure 4:
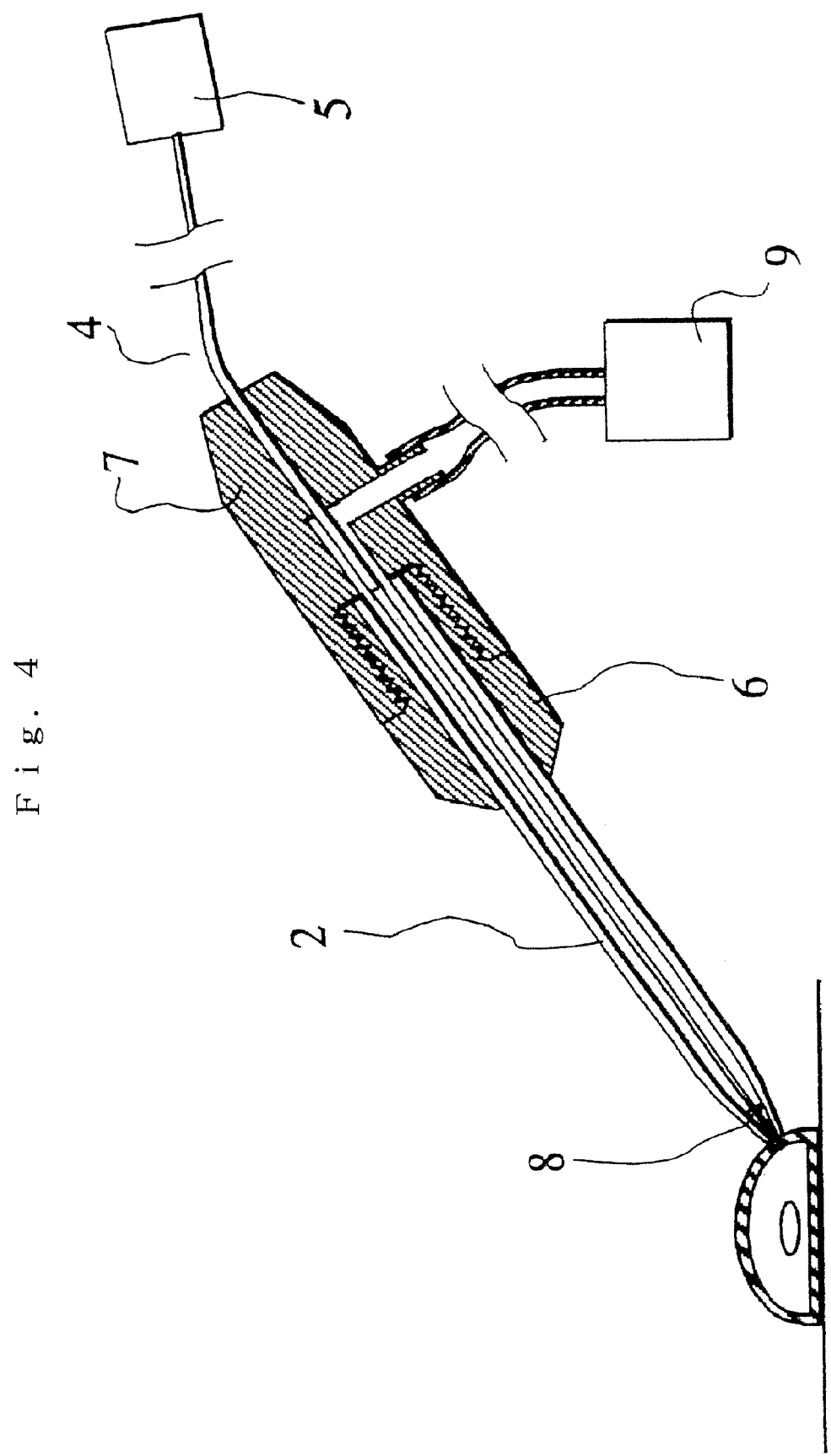
FIG. 4 is a schematic view showing another preferred embodiment of a microinjection apparatus.
Figure 5:
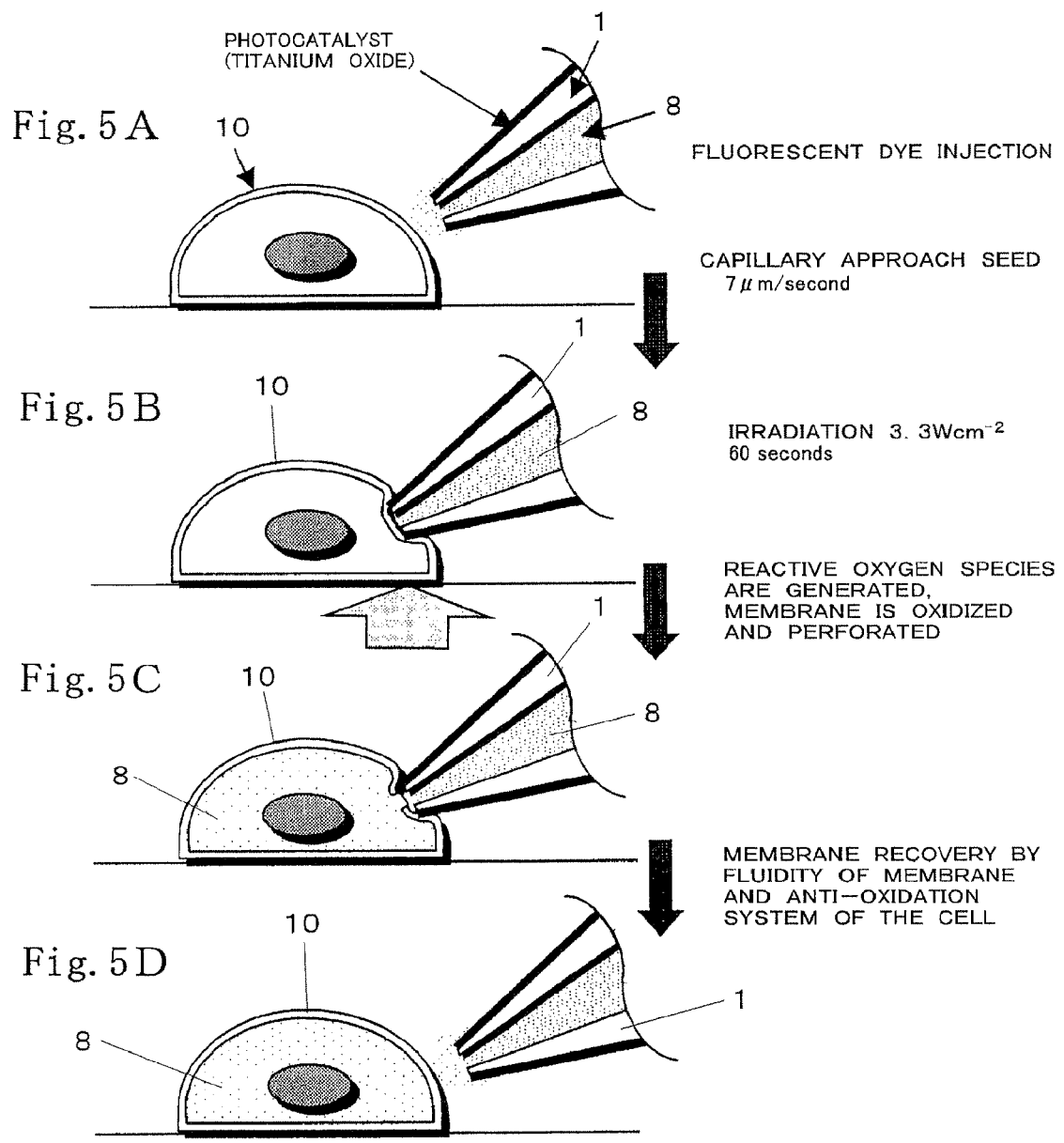
FIGS. 5A-D are schematic views showing a process of injecting a water-soluble fluorescent dye agent into a cell.

FIG. 4 is a schematic view showing another preferred embodiment of a microinjection apparatus employing the present invention. According to the embodiment, similar to the first embodiment, the light is selected as the stimulus, and the photosensitizer agent is selected as the membrane-denaturing agent.

In the embodiment, inside the capillary 2, an optical fiber 4 extends in the length of the capillary 2 centrally. A distal end of the fiber 4 extends to the tip of the capillary 2. According to this configuration, the light, as the stimulus, transmits through the optical fiber 4 and is applied to the photosensitizer in contact with the membrane so that the substance to be injected such as genes is not badly affected.

FIGS. 5A-D show still another embodiment of the present invention. According to this embodiment, photocatalyst is provided on outer surface of the sidewall of the capillary 1 and the photocatalyst is activated by the irradiation. In one preferable example, the photocatalyst is titanium oxide, and the irradiation as the stimulus is selected from the lights having a wavelength activating the titanium oxide. A site to be covered by the photocatalyst is the tip of the capillary, especially a site to be in contact with the membrane. In the figures, an injection liquid 8 containing a water-soluble fluorescent dye (Lucifer Yellow CH 2 millimolar concentration) is injected into a cell of the established neuron-like cell line PC 12. PC12 cells are used as a model of the central nervous system and are ganglia-like cells of Rat adrenal medulla origin. The cell is temporarily oxidized by the photocatalyst to denature the property of the cell, and then it is possible to penetrate the cell membrane 10 by contacting the capillary with the surface of the cell even at a low speed.

Figure 6:
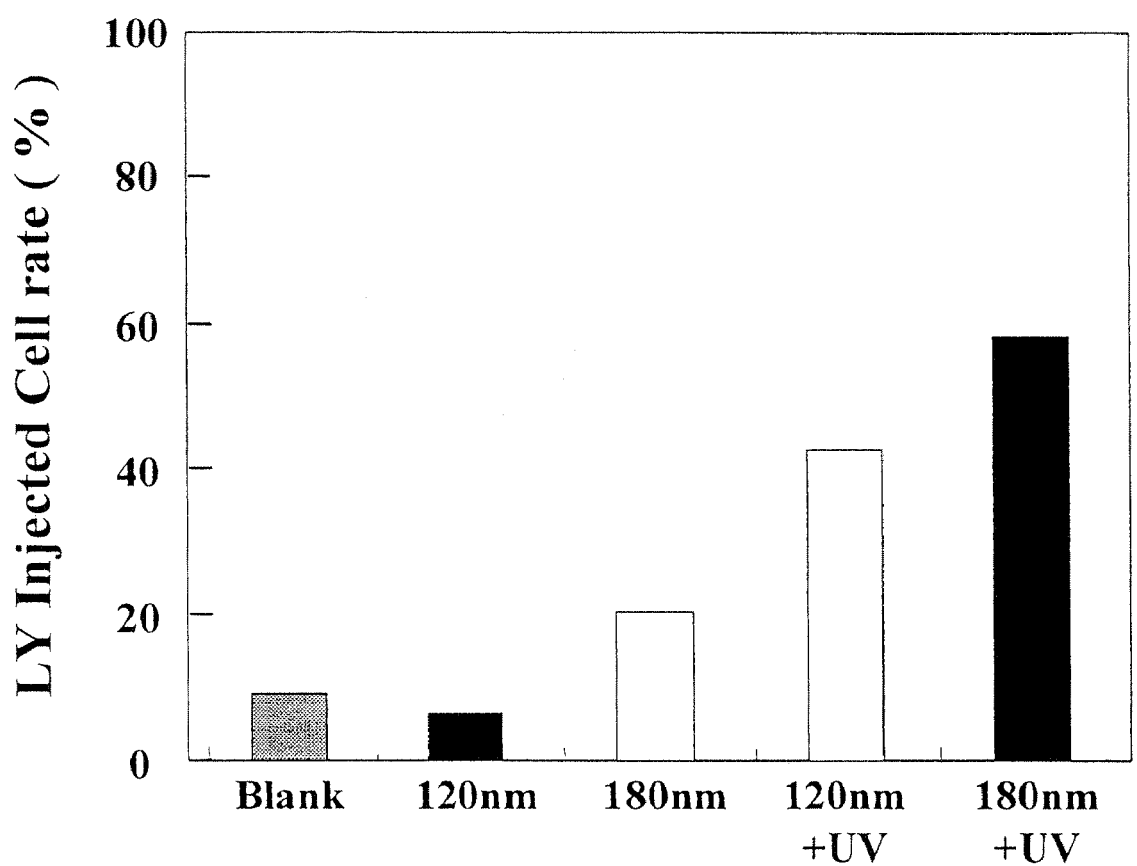
FIG. 6 is a graph showing a success rate of injection in which blank: capillary without a titanium oxide film; 120 nm: capillary with a 120 nm-thick titanium oxide film, 180 nm: capillary with a 180 nm-thick titanium oxide film; and UV: one-minute ultraviolet ray exposure.

FIG. 6 shows the success rate of the injection with regard to the thickness of titanium oxide film formed on the sidewall of the capillary. An aim of the FIG. 6 is to show the effect of the photocatalyst and the data in FIG. 6 was obtained by directly applying the light to the capillary and not by applying the light through the wall of the capillary as the light guide. Under such approach conditions where the membrane perforation by the physical force is difficult, the success rate of injection using the photosensitizing mechanism was compared. During the injection operation, the moving range of the manipulator was set so that it is possible for the capillary to penetrate into the cell at the speed of 1000 micrometers/s. Then, the capillary was approached at the low speed of 7 micrometers/s to contact the cell membrane without mechanically perforating the cell membrane. In the experiments, comparative tests as to how the success rate of the injection is changed with/without titanium oxide film on the capillary, and with/without one-minute light exposure by the 100 W mercury ramp were conducted.

The results are shown in FIG. 6. In FIG. 6, the horizontal axis indicates the injection treatment conditions, and the vertical axis shows the success rate of the injection (unit:%). When the capillary was not coated with the titanium oxide, the success rate of the injection was about 10%. On the other hand, when the capillary was coated with titanium oxide of 120 nanometers thickness, the success rate was 40% with one-minute ultraviolet ray exposure. Also, when the capillary was coated with titanium oxide of 120 nanometers thickness without the light exposure, the success rate of the injection was about 10%, and an improvement was not recognized. When the capillary was coated with titanium oxide of 180 nanometers thickness, the success rate of the injection was 60% with one-minute ultraviolet ray exposure. Also, even without the light exposure, the success rate of the injection was about 20%. Presumably, it is because the photocatalyst was activated by the room light, thereby improving the success rate of the injection.

According to the conducted microinjection experiment, the success rate of the injection was about 20%, without coating the capillary with titanium oxide, or without the ultraviolet ray exposure. Compared to this effort, the success rate of the injection was about 60% at maximum with the use of titanium oxide and the light exposure. It means that the titanium oxide facilitated the perforation of the cell membrane with the ultraviolet ray exposure. It is said that the photocatalytic activation of titanium oxide proportionally increases relative to the thickness of the film up to 2 micrometers. The present test also shows that the success rate of the injection becomes higher with the thicker film. The test strongly suggests that the photocatalytic activation was effective for improving the efficiency of the microinjection.

Industrial Applicability

According to the present invention, due to the membrane denaturation, it is possible to conduct membrane perforation with such a weak shear force as exerted when the capillary contacts the cell membrane, thereby allowing the perforation of the membrane without depending on the physical shear force. Therefore, the present invention can be used for the microinjection apparatus and such. In one preferred application, the present invention is used for introducing genes into the cells.

The embodiments of the invention in which an exclusive property or privilege is claimed are defined as follows:

1. A cell membrane perforating apparatus comprising:
   an ultraviolet light source;
   a photosensitizer or photocatalyst as a membrane-denaturing substance that induces a temporarily membrane-denaturing reaction when irradiated with ultraviolet light wherein said temporarily membrane-denaturing reaction is obtained by chain peroxidation of the membrane with generation of reactive oxygen species by combination with said photosensitizer or photocatalyst and ultraviolet light; and
   a membrane-perforating member that has a tip having a size sufficiently small to penetrate the membrane of a singular cell, supports said photosensitizer or photocatalyst so as to bring said photosensitizer or photocatalyst in contact with or close proximity to a portion of said membrane of the singular cell and carries the light supplied by said ultraviolet light source therethrough to irradiate said photosensitizer or photocatalyst supported by said membrane-perforating member to induce said temporarily membrane-denaturing reaction at said portion of the membrane of the singular cell;
   wherein said membrane-perforating member is configured to be moveable at a speed sufficiently low to contact and penetrate a denatured portion of said membrane of the singular cell without causing cell death.

2. The apparatus according to claim 1, said apparatus further comprising an electric power source or heat supply, wherein said membrane-perforating member comprises an ultraviolet light emitting element as said ultraviolet light source for converting the power or heat received from said power source or heat supply into the ultraviolet light.

3. The apparatus according to claim 1, wherein said membrane-perforating member is a capillary.

4. The apparatus according to claim 3, wherein said ultraviolet light transmits through the sidewall of said capillary as an ultraviolet light guide.

5. The apparatus according to claim 3, wherein at least one optical fiber extends in the length of said capillary, said fiber is provided inside and/or outside of the capillary, and a distal end of said fiber extends to the tip of said capillary so as to apply said ultraviolet light to said photosensitizer or photocatalyst from the end of said fiber.

6. A microinjection apparatus comprising the membrane perforating apparatus as claimed in claim 1, wherein said microinjection apparatus injects a desired substance inside the membrane.

7. The microinjection apparatus according to claim 6, wherein said membrane-perforating member is a capillary.

8. The microinjection apparatus according to claim 6, wherein said substance contains a photosensitizer or photocatalyst as a membrane denaturing substance that induces a membrane-denaturing reaction by ultraviolet light as a stimulus.

9. The microinjection apparatus according to claim 8, wherein said substance further includes an additional substance that is selected from the group comprising nucleic acids, proteins, lipids, membrane structures, micro machines, and magnetic particles.

10. The apparatus according to claim 1, wherein said membrane-perforating member is an intracellular sensor.

11. The apparatus according to claim 1, wherein said membrane-perforating members comprise a plurality of needle-shaped, rod-shaped, or tube-shaped members.

12. The apparatus according to claim 11, wherein said membrane-perforating members comprise capillaries and/or intracellular sensors.

13. The microinjection apparatus according to claim 6, wherein said membrane-perforating members comprise a plurality of needle-shaped, rod-shaped, or tube-shaped members.

14. The microinjection apparatus according to claim 13, wherein said membrane-perforating members comprise capillaries and/or intracellular sensors.

15. An apparatus for denaturing a portion of cell membrane,
an ultraviolet light source:
a photosensitizer or photocatalyst as a membrane-denaturing substance that induces a temporarily membrane-denaturing reaction when irradiated with ultraviolet light: and
a support member that has a tip having a size sufficiently small to contact a portion of a membrane of a singular cell, and said support member configured to support said membrane-denaturing substance at least at said tip so as to bring said membrane-denaturing substance in contact with or close proximity to said portion of the membrane of a singular cell and to carry the ultraviolet light supplied by said ultraviolet source therethrough to irradiate said membrane-denaturing substance supported by said tip of the support member to induce said temporarily membrane-denaturing reaction at said portion of the membrane to obtain a denatured portion on said portion of the membrane of the singular cell.

16. The apparatus according to claim 15, wherein said support member comprises a plurality of tips.

17. The apparatus according to claim 15, wherein said support member perforates said denatured portion of the membrane with said tip.

18. The apparatus according to claim 1, wherein said tip is configured with a passageway to enable the photosensitizer or photocatalyst to flow through the tip and deliver the photosensitizer or photocatalyst into contact with or close proximity to the portion of said cell membrane and is configured to transmit the ultraviolet light through said tip to irradiate the photosensitizer or photocatalyst being into contact with or close proximity to said portion of said cell membrane.

* * * * *